(12) United States Patent
Vanderbilt et al.

(10) Patent No.: US 7,832,856 B2
(45) Date of Patent: *Nov. 16, 2010

(54) COATINGS AND SOLUTIONS FOR CONTACT LENSES

(75) Inventors: David P. Vanderbilt, Webster, NY (US); Daniel M. Ammon, Jr., Webster, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 292 days.

This patent is subject to a terminal disclaimer.

(21) Appl. No.: 11/872,305

(22) Filed: Oct. 15, 2007

(65) Prior Publication Data

US 2008/0151180 A1 Jun. 26, 2008

Related U.S. Application Data

(60) Provisional application No. 60/870,854, filed on Dec. 20, 2006.

(51) Int. Cl.
G02C 7/04 (2006.01)
B32B 9/04 (2006.01)

(52) U.S. Cl. .............. 351/160 R; 351/160 H; 428/411.1; 428/427

(58) Field of Classification Search ............. 351/160 R, 351/160 H
See application file for complete search history.

(56) References Cited

U.S. PATENT DOCUMENTS

| | | | |
|---|---|---|---|
| 4,136,250 A | 1/1979 | Mueller et al. |
| 4,153,641 A | 5/1979 | Deichert et al. |
| 4,634,722 A | 1/1987 | Gallop |
| 4,740,533 A | 4/1988 | Su et al. |
| 4,910,277 A | 3/1990 | Bambury et al. |
| 5,034,461 A | 7/1991 | Lai et al. |
| 5,070,215 A | 12/1991 | Bambury et al. |
| 5,260,000 A | 11/1993 | Nandu et al. |
| 5,310,779 A | 5/1994 | Lai |
| 5,346,976 A | 9/1994 | Ellis et al. |
| 5,358,995 A | 10/1994 | Lai et al. |
| 5,387,662 A | 2/1995 | Kunzler et al. |
| 5,407,919 A | 4/1995 | Brode et al. |
| 5,449,729 A | 9/1995 | Lai |
| 5,512,205 A | 4/1996 | Lai |
| 5,595,980 A | 1/1997 | Brode et al. |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler et al. |
| 5,908,906 A | 6/1999 | Kunzler et al. |
| 5,985,629 A | 11/1999 | Aaslyng et al. |
| 6,190,751 B1 | 2/2001 | Sylvester |
| 6,200,626 B1 | 3/2001 | Grobe et al. |
| 6,213,604 B1 | 4/2001 | Valint, Jr. et al. |
| 6,348,508 B1 | 2/2002 | Denick, Jr. et al. |
| 6,440,366 B1 | 8/2002 | Salpekar et al. |
| 6,440,571 B1 | 8/2002 | Valint, Jr. et al. |
| 6,478,423 B1* | 11/2002 | Turner et al. ............. 351/177 |
| 6,550,915 B1 | 4/2003 | Grobe, III |
| 6,589,665 B2 | 7/2003 | Chabrecek et al. |
| 6,649,722 B2 | 11/2003 | Rosenzweig et al. |
| 6,794,456 B2 | 9/2004 | Grobe, III |
| 6,815,074 B2 | 11/2004 | Aguado et al. |
| 6,891,010 B2 | 5/2005 | Kunzler et al. |
| 2004/0006385 A1 | 1/2004 | Valint, Jr. et al. |
| 2004/0063591 A1 | 4/2004 | Borazjani et al. |
| 2004/0063620 A1 | 4/2004 | Xia et al. |
| 2005/0171232 A1 | 8/2005 | Ford et al. |
| 2007/0030443 A1* | 2/2007 | Chapoy et al. .......... 351/160 R |
| 2007/0116740 A1 | 5/2007 | Valint, Jr. et al. |

FOREIGN PATENT DOCUMENTS

| | | |
|---|---|---|
| WO | WO99/10022 | 3/1999 |
| WO | WO03/096876 | 11/2003 |
| WO | WO2005/000109 | 1/2005 |
| WO | WO2005/015184 | 2/2005 |

OTHER PUBLICATIONS

Otsuka et al., "Anomalous Binding Profile of Phenylboronic Acid with N-Acetylneuraminic Acid (Neu5Ac) in Aqueous Solution with Varying pH," Journal of American Chemical Society, vol. 125 (No. 12), p. 3493-3502, (Feb. 27, 2003).

Kikuchi et al., "Glucose-Sensing Electrode Coated with Polymer Complex Gel Containing Phenylboronic Acid," Analytical Chemistry, vol. 68 (No. 5), p. 823-828, (Mar. 1, 1996).

Springsteen et al., "A Detailed Examination of Boronic Acid-diol Complexation," Tetrahedron, 2002, 58, 5291-5300.

Sears et al., "Enzyme Action in Glycoprotein Synthesis," CMLS, 1998, 54, 223-252.

Danjo et al., "Alteration of Mucin in Human Conjunctival Epithelia in Dry Eye," Investigative Ophthalmology and Visual Science, 1988, 39(13), 2602-2609.

Vanderbilt, et al., "Coatings and Solutions for Contact Lenses," U.S. Appl. No. 11/876,881, filed Oct. 23, 2007.

* cited by examiner

Primary Examiner—Jordan M. Schwartz
(74) Attorney, Agent, or Firm—John E. Thomas

(57) ABSTRACT

A contact lens is coated with a first polymer, such as a boronic acid-containing copolymer, having affinity to mucin, and a second polymer. The second polymer improves initial comfort of the contact lens. During wear of the contact lens, the second polymer is removed from the contact lens, by blinking and/or tear fluids, and mucin complexes with the first polymer on the contact lens surface.

24 Claims, No Drawings

COATINGS AND SOLUTIONS FOR CONTACT LENSES

BACKGROUND OF THE INVENTION

Mucins are glycoconjugated proteins which are secreted by vesicles and discharged on the surface of the conjunctival epithelium of the eye. Mucins are found on moist, mucosal epithelia, and are thought to combine mechanical protection of eye tissue as well as chemical and immune protection of mucosal tissue. The surface of the eye is kept moist and lubricated by tear film. Mucins anchor this tear film to the epithelium and protect the eye surface from bacterial, chemical and physical invasion of foreign bodies.

U.S. Pat. Nos. 6,348,508 (Denick, Jr. et al.), 2004/0063620 (Xia et al.), and 2004/0063591 (Borazjani et al.) disclose compositions for treating dry eye or for treating contact lenses that comprise a cationic polysaccharide. In the case of eye drop solutions, the cationic polysaccharides, after binding to the mucosal eye tissue, may in turn promote the mucins in the eye, either by supplementing the mucin and/or by helping to bind and maintain mucin on the eye surface.

In the case of contact lenses, mucins are often viewed as a debris that, like other proteins, should not accumulate on the contact lens surface. For example, U.S. Pat. No. 5,985,629 (Aaslyng et al.) discloses contact lens cleaning and disinfecting compositions comprising an enzyme and an enzyme inhibitor. Aryl boronic acids are mentioned as a possible enzyme inhibitor and/or disinfectant, but the purpose of the compositions is to remove soil deposits from a contact lens, such soil deposits including mucin (at column 1). As another example, U.S. Pat. No. 6,649,722 (Rosenzweig et al.) discloses contact lens compositions. At column 28, it is reported that binding of mucin to the lens was at a desirably low enough level that the mucin would not lead to corneal adhesion of the lens.

Blister packages and glass vials are typically used to individually package each soft contact lens for sale to a customer. Saline or deionized water is commonly used to store the lens in the packages, as mentioned in various patents related to the packaging or manufacturing of contact lenses. Because lens material may tend to stick to itself and to the lens package, packaging solutions for blister-packs have sometimes been formulated to reduce or eliminate lens folding and sticking; packaging solutions may include a polymer to improve comfort of the contact lens. Polyvinyl alcohol (PVA) has been used in contact lens packaging solutions. Additionally, U.S. Pat. No. 6,440,366 discloses contact lens packaging solutions comprising polyethylene oxide (PEO)/polypropylene oxide (PPO) block copolymers, especially poloxamers or poloxamines.

SUMMARY OF THE INVENTION

This invention provides a method that comprises treating a contact lens with a solution comprising: a first polymer comprising moieties that complex with mucin; and a second polymer different from the first polymer.

This invention also provides a contact lens having its surfaces coated with an inner layer and an outer layer, the inner layer comprising a first polymer having affinity for mucin, and the outer layer comprising a second polymer different from the first polymer. The contact lens may further comprise a layer intermediate to the inner layer and the contact lens surface and containing a third polymer different from the first and second polymers, or the inner layer may be directly linked to the contact lens surface.

According to other embodiments, the contact lens is packaged in a solution comprising different first and second polymers, where the first polymer comprises moieties that are able to complex with mucin.

According to further embodiments, the invention provides a method comprising: placing in a contact lens package a contact lens and a solution comprising different first and second polymers, the first polymer comprising moieties that are able to complex with mucin; sealing the package with lidstock; and autoclaving the package and its contents.

According to various preferred embodiments, the first polymer has greater affinity to mucin than to the second polymer, and greater affinity to surfaces of the contact lens than does the second polymer. The second polymer is adsorbed on the contact lens coated with the first polymer.

The first polymer may comprise monomeric units derived from an ethylenically unsaturated monomer containing a boronic acid moiety. Such boronic acid-containing polymers may further include monomeric units derived from an ethylenically unsaturated monomer containing a tertiary-amine moiety, monomeric units derived from an ethylenically unsaturated monomer containing a hydrophilic moiety in an amount sufficient to render the first polymer water soluble, and/or monomeric units derived from an ethylenically unsaturated monomer containing a moiety reactive with complementary reactive functionalities at the lens surface.

It is preferred the second polymer, or the layer containing the second polymer, is non-permanently bound to the contact lens, and is removed from the inner layer while the contact lens is worn. Upon removal of the second polymer during wear of the contact lens, the first polymer, comprising moieties such as boronic acid moieties, complex with mucin. It is preferred the first polymer is permanently bound to the contact lens, and the second polymer is temporarily bound to the contact lens.

DETAILED DESCRIPTION

This invention is useful for contact lenses which, when worn, are in contact with epithelial tissue. This invention is useful for all known types of contact lenses, including both soft and rigid lens materials. Hydrogels represent one class of materials used for contact lens applications. Hydrogels comprise a hydrated, cross-linked polymeric system containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer may function as a crosslinking agent (a crosslinking agent being defined as a monomer having multiple polymerizable functionalities), or alternately, a separate crosslinking agent may be employed in the initial monomer mixture from which the hydrogel copolymer is formed. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) Silicone hydrogels typically have a water content between about 10 to about 80 weight percent.

Examples of useful lens-forming hydrophilic monomers include: amides such as N,N-dimethylacrylamide and N,N-dimethylmethacrylamide; cyclic lactams such as N-vinyl-2-pyrrolidone; (meth)acrylated alcohols, such as 2-hydroxyethyl methacrylate and 2-hydroxyethylacrylate; and (meth) acrylated poly(ethyleneglycol)s; and azlactone-containing monomers, such as 2-isopropenyl-4,4-dimethyl-2-oxazolin-5-one and 2-vinyl-4,4-dimethyl-2-oxazolin-5-one. (As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid.) Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art.

As mentioned, one preferred class hydrogel contact lens materials is silicone hydrogels. In this case, the initial lens-forming monomer mixture further comprises a silicone-containing monomer.

Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomers include bulky polysiloxanylalkyl(meth)acrylic monomers. An example of bulky polysiloxanylalkyl(meth)acrylic monomers are represented by the following Formula I:

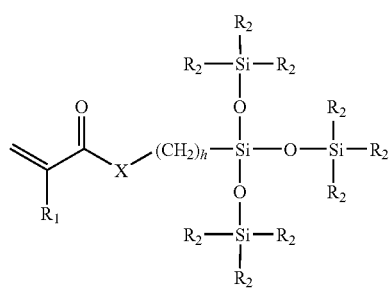

(I)

wherein:

X denotes —O— or —NR—;

each $R_1$ independently denotes hydrogen or methyl;

each $R_2$ independently denotes a lower alkyl radical, phenyl radical or a group represented by

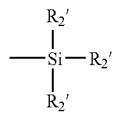

wherein each $R_2'$ independently denotes a lower alkyl or phenyl radical; and h is 1 to 10. One preferred bulky monomer is methacryloxypropyl tris(trimethylsiloxy)silane or tris(trimethylsiloxy)silylpropyl methacrylate, sometimes referred to as TRIS.

Another class of representative silicon-containing monomers includes silicone-containing vinyl carbonate or vinyl carbamate monomers such as: 1,3-bis[4-vinyloxycarbonyloxy)but-1-yl]tetramethyl-disiloxane; 1,3-bis[4-vinyloxycarbonyloxy)but-1-yl]polydimethylsiloxane; 3-(trimethylsilyl)propyl vinyl carbonate; 3-(vinyloxycarbonylthio)propyl-[tris(trimethylsiloxy)silane]; 3-[tris(trimethylsiloxy)silyl] propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula II:

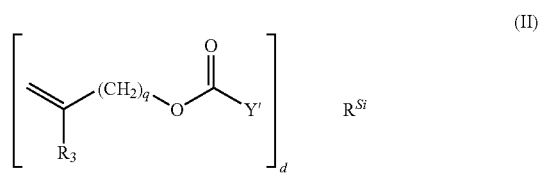

(II)

wherein:

Y' denotes —O—, —S— or —NH—;

$R^{Si}$ denotes a silicone-containing organic radical;

$R_3$ denotes hydrogen or methyl;

d is 1, 2, 3 or 4; and q is 0 or 1.

Suitable silicone-containing organic radicals $R^{Si}$ include the following:

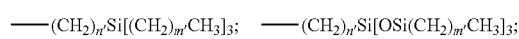

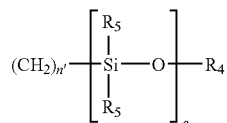

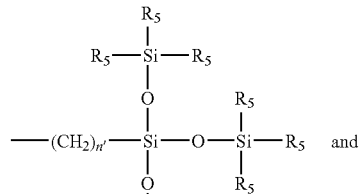
and

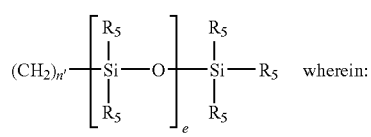
wherein:

$R_4$ denotes

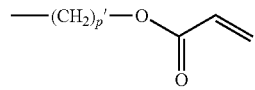

wherein p' is 1 to 6;

$R_5$ denotes an alkyl radical or a fluoroalkyl radical having 1 to 6 carbon atoms;

e is 1 to 200; n' is 1, 2, 3 or 4; and m' is 0, 1, 2, 3, 4 or 5.

An example of a particular species within Formula II is represented by Formula III:

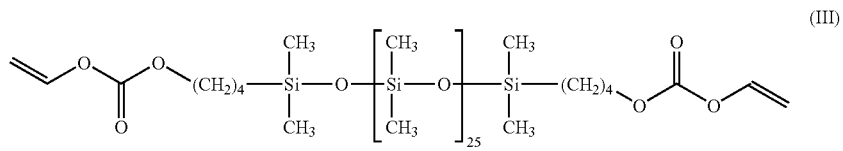
(III)

Another class of silicon-containing monomers includes polyurethane-polysiloxane macromonomers (also sometimes referred to as prepolymers), which may have hard-soft-hard blocks like traditional urethane elastomers. Examples of silicone urethane monomers are represented by Formulae IV and V:

$$E(*D*A*D*G)_a*D*A*D*E'; \text{ or} \qquad (IV)$$

$$E(*D*G*D*A)_a*D*G*D*E'; \qquad (V)$$

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula VI:

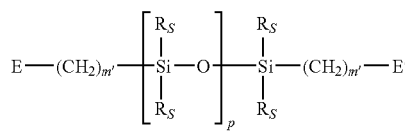
(VI)

wherein:
each $R_s$, independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula VII:

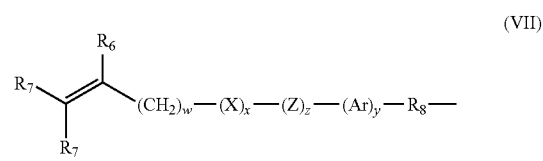
(VII)

wherein:

$R_6$ is hydrogen or methyl;

$R_7$ is hydrogen, an alkyl radical having 1 to 6 carbon atoms, or a —CO—Y—$R_9$ radical wherein Y is —O—, —S— or —NH—;

$R_8$ is a divalent alkylene radical having 1 to 10 carbon atoms;

$R_9$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6; x is 0 or 1; y is 0 or 1; and z is 0 or 1.

A more specific example of a silicone-containing urethane monomer is represented by Formula (VIII):

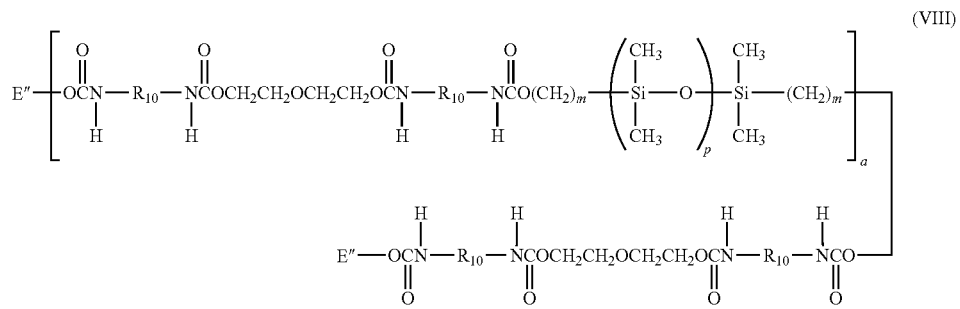
(VIII)

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate group, such as the diradical of isophorone diisocyanate, and each E'' is a group represented by:

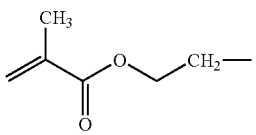

A preferred silicone hydrogel material comprises (based on the initial monomer mixture that is copolymerized to form the hydrogel copolymeric material) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

An additional class of contact lens materials are rigid copolymers, especially rigid, gas-permeable (RGP) copolymers. RGP copolymers generally include: a silicone-containing monomer, including any of the aforementioned silicone-containing monomers mentioned above; a hydrophilic monomer as a wetting agent; a hardness modifying monomer; and a crosslinking agent; a polymerization initiator; an ultra-violet blocking agent; or a colorant.

Specific examples of contact lens materials useful in the present invention are taught in U.S. Pat. Nos. 6,891,010 (Kunzler et al.); 5,908,906 (Kunzler et al.); 5,714,557 (Kunzler et al.); 5,710,302 (Künzler et al.); 5,708,094 (Lai et al.); 5,616,757 (Bambury et al.); 5,610,252 (Bambury et al.); 5,512,205 (Lai); 5,449,729 (Lai); 5,387,662 (Kunzler et al.); 5,310,779 (Lai); 5,260,000 (Nandu et al.); and 5,346,976 (Ellis et al.); the disclosures of which are incorporated herein by reference.

The first polymer links to the contact lens surface and contains a moiety that complexes, or forms a complex, with mucin. Boronic acid groups complex readily with sialic acid carbohydrate residues at physiological pH (7.4). Because mucins contain substantial amounts of sialic acid residues in their polysaccharide side chains, boronic acid groups should have an affinity for mucins. Accordingly, a preferred class of polymers with affinity for mucin are polymers containing a boronic acid moiety. Boronic acid ($-B(OH)_2$) groups are able to complex with the polysaccharide side chains found in mucin, and thereby possess an affinity for the mucins in tear fluid while the contact lens is worn.

The polymers may comprise monomeric units derived from an ethylenically unsaturated monomer containing the boronic acid moiety. Examples are ethylenically unsaturated aryl boronic acids, such as: 4-vinylphenylboronic acid; and 3-methacrylamidophenylboronic acid.

The boronic acid-containing polymers may include, in addition to the monomeric units derived from an ethylenically unsaturated monomer containing the boronic acid moiety, a monomeric unit derived from an ethylenically unsaturated monomer containing a reactive moiety. Specifically, the ethylenic unsaturation of this monomer renders the monomer copolymerizable with the boronic acid-containing monomer. In addition, this monomer contains the reactive moiety that is reactive with complementary reactive functionalities at the lens surface, and/or complementary reactive functionalities of an intermediate polymer, discussed in more detail below.

Examples of reactive monomers include: ethylenically unsaturated carboxylic acids, such as (meth)acrylic acid; ethylenically unsaturated primary amines, such as 2-aminoethyl (meth)acrylate, N-(2-aminoethyl)(meth)acrylamide, 3-aminopropyl (meth)acrylate, and N-(3-aminopropyl)(meth)acrylamide; alcohol-containing (meth)acrylates and (meth)acrylamides, such as 2-hydroxyethyl methacrylate; ethylenically unsaturated epoxy-containing monomers, such as glycidyl methacrylate or glycidyl vinyl carbonate; and azlactone-containing monomers, such as 2-isopropenyl-4,4-dimethyl-2-oxazolin-5-one and 2-vinyl-4,4-dimethyl-2-oxazolin-5-one, where the azlactone group hydrolyzes in aqueous media to convert the oxazolinone moiety to a reactive carboxylic acid moiety.

The polymers may further include a monomeric unit containing a tertiary-amine moiety. Generally, diols complex most readily with mucins at a basic pH. By including this monomeric unit in the polymer, it is believed the boronic acid will complex more readily with mucin at physiological pH. Examples of monomers copolymerizable with the boronic acid monomer are ethylenically unsaturated monomers containing the tertiary-amine moiety. Specific examples include: 2-(N,N-dimethyl)ethylamino(meth)acrylate, N-[2-(dimethylamino)ethyl](meth)acrylamide, N-[(3-dimethylamino)propyl](meth)acrylate, N-[3-dimethylamino)propyl](meth)acrylamide and vinylbenzyl-N,N-dimethylamine.

The polymers may further include a hydrophilic monomeric unit. Examples include ethylenically unsaturated monomers that are copolymerizable with the boronic acid ethylenically unsaturated monomer. Specific examples include: N,N-dimethylacrylamide and N,N-dimethylmethacrylamide; cyclic lactams such as N-vinyl-2-pyrrolidone; (meth)acrylated alcohols, such as 2-hydroxyethyl methacrylate and 2-hydroxyethyl acrylate; and (meth)acrylated poly(ethyleneglycol)s. The main purpose of the hydrophilic monomeric unit in the polymer, when used, is to ensure the polymer is water-soluble, thus avoiding the need to dissolve the polymer in organic solvent when applying the polymer to the lens surface.

Accordingly, one class of preferred polymers are copolymers comprising: monomeric units derived from an ethylenically unsaturated monomer containing a boronic acid moiety; and monomeric units derived from an ethylenically unsaturated monomer containing a moiety reactive with complementary reactive functionalities at the lens surface. These copolymers may further include: monomeric units derived from the ethylenically unsaturated monomer containing the tertiary-amine moiety; and monomeric units derived from an ethylenically unsaturated hydrophilic monomer in an amount sufficient to render the copolymer water soluble. This class of copolymers may comprise: 1 to 30 mole percent of the boronic acid-containing monomeric units, more preferably 2 to 20 mole percent; and 2 to 50 mole percent of monomeric units derived from an ethylenically unsaturated monomer containing the moiety reactive with complementary reactive functionalities at the lens surface, more preferably 5 to 40 mole percent. Preferably, these copolymers comprise: 0 to 50 mole percent of the tertiary-amine-containing monomeric units, more preferably 5 to 40 mole percent; and 0 to 90 mole percent of the hydrophilic monomeric units, more preferably 20 to 80 mole percent.

Another class of preferred polymers are copolymers comprising: monomeric units derived from an ethylenically unsaturated monomer containing a boronic acid moiety; monomeric units derived from the ethylenically unsaturated monomer containing the tertiary-amine moiety; and monomeric units derived from an ethylenically unsaturated hydrophilic monomer in an amount sufficient to render the copolymer water soluble. This class of copolymers may comprise: 1 to 30 mole percent of the boronic acid-containing monomeric units, more preferably 2 to 20 mole percent; and 2 to 50 mole percent of monomeric units derived from the ethylenically unsaturated tertiary-amine-containing monomeric units, more preferably 5 to 40 mole percent; and 10 to 90 mole percent of the hydrophilic monomeric units, more preferably 20 to 80 mole percent.

As mentioned, the copolymers may include monomeric units derived from an ethylenically unsaturated monomer containing a reactive moiety, and in this case, this reactive moiety links the polymer to the lens surface. One manner of linking the boronic acid-containing polymer to the lens surface involves forming the lens from a monomer mixture including a monomer that includes reactive functionalities that are complementary with the reactive moiety of the polymer.

As a first example, the contact lens may be formed of the polymerization product of a monomer mixture comprising an epoxy-containing monomer, such as glycidyl methacrylate or glycidyl vinyl carbonate. Sufficient epoxy groups will migrate to the lens surface, and these epoxy groups covalently react with functionalities of the boronic acid-containing polymer, especially carboxylic acid, amino and alcohol reactive moieties.

As a second example, the contact lens may be formed of the polymerization product of a monomer mixture comprising a carboxylic acid-containing monomer, such as (meth)acrylic acid or vinyl carbonic acid. Sufficient carboxylic groups will be present at the lens surface to covalently react with functionalities of the boronic acid-containing polymer, especially amino and alcohol reactive moieties.

As a third example, the contact lens may be formed of the polymerization product of a monomer mixture comprising an azlactone-containing monomer, such as 2-isopropenyl-4,4-dimethyl-2-oxazolin-5-one and 2-vinyl-4,4-dimethyl-2-oxazolin-5-one. Azlactone groups at the lens surface will hydrolyze in aqueous media to convert the oxazolinone group to a carboxylic acid, for reaction with the boronic acid-containing polymer reactive moieties.

As another example, the contact lens may be formed of the polymerization product of a monomer mixture comprising a (meth)acrylate or (meth)acrylamide alcohol, such as 2-hydroxyethyl methacrylate. The alcohol groups are available to react with boronic acid-containing polymer reactive moieties.

Other lens-forming monomers containing complementary reactive groups are known in the art, including those disclosed in U.S. Pat. No. 6,440,571 (Valint, Jr. et al.), the entire disclosure of which is incorporated herein by reference.

Another manner of linking the boronic acid-containing polymer to the lens surface involves treating the lens surface to provide reactive functionalities that are complementary with the reactive moiety of the polymer. As an example, the lens surface may be subjected to plasma treatment in an oxygen-containing atmosphere to form alcohol functionalities on the lens surface, or in a nitrogen-containing atmosphere to form amine functionalities on the lens surface. In the case that the contact lens contains fluorine at its surface, the lens surface may be initially plasma treated in a hydrogen atmosphere to reduce fluorine content at the lens surface.

Such methods are known in the art, including U.S. Pat. Nos. 6,550,915 and 6,794,456 (Grobe III), the entire disclosures of which are incorporated herein by reference.

The alcohol or amino functionality generated at the lens surface by the plasma treatment may then react with reactive moieties of the boronic acid-containing polymer, especially carboxylic acid moieties.

A variation of plasma treatment involves initially subjecting the lens surface to a plasma oxidation, followed by plasma polymerization in an atmosphere containing a hydrocarbon (such as a diolefin, for example, 1,3-butadiene) to form a carbon layer on the lens surface. Then, this carbon layer is plasma treated in an oxygen or nitrogen atmosphere to generate hydroxyl or amine radicals. The reactive moiety of the boronic acid-containing polymer can then be covalently attached to the hydroxyl or amine radicals of the carbon layer. This method is disclosed in U.S. Pat. No. 6,213,604 (Valint, Jr. et al.), the entire disclosure of which is incorporated herein by reference.

In the case of silicone hydrogel contact lenses, the lenses may be plasma treated in an oxygen-containing atmosphere to form a silicate-containing surface on the lens, which surface then binds the boronic acid-containing polymer.

As used herein, the term "plasma treatment" is inclusive of wet or dry corona discharge treatments.

Another manner of linking the boronic acid-containing polymer to the lens surface involves employing an intermediate polymer. More specifically, the intermediate polymer is linked to both the boronic acid-containing polymer and the lens surface. Thus, this intermediate polymer has functionality reactive with the lens surface, as well as functionality reactive with the reactive moieties of the boronic acid-containing polymer.

This intermediate polymer may be covalently linked to the lens surface by the various methods, discussed supra in relation to direct linking of the boronic acid-containing polymer. For example, the contact lens may be formed of a monomer mixture including a monomer that includes reactive functionalities that are complementary with the reactive functionalities of the intermediate polymer. Alternately, the contact lens surface may be treated, for example, plasma treated, to provide reactive sites for the intermediate polymer The intermediate polymer may be covalently linked to the boronic acid-containing polymer by providing both polymers with complementary reactive groups, including those mentioned supra. Additional examples are found in U.S. Pat. No. 6,440,571 (Valint, Jr. et al.).

As an example, the lens may be coated with a mixture of an intermediate copolymer of N,N-dimethylacrylamide and glycidyl methacrylate, and a boronic acid-containing copolymer. The epoxy functionality of the intermediate copolymer will covalently link to hydroxyl, primary amine or carboxylic acid moieties at the lens surface, and will covalently link to hydroxyl, primary amine or carboxylic acid moieties of the boronic acid-containing polymer. Numerous other examples of intermediate polymers are evident.

Accordingly, various methods generally known in the art are available for linking the boronic acid-containing polymer to the contact lens surface. Other methods will be evident to ones skilled in the art.

For this invention, the polymer having mucin affinity, for example, the boronic acid-containing polymer, is included in the aqueous solution in which the contact lens is packaged. Preferred packages are glass vials sealable with lidstock, or plastic blister packages including a recess for receiving a contact lens and the packaging solution, where the recess is sealed with lidstock prior to sterilization of the package contents. Sterilization preferably occurs after sealing of the package with lidstock, and preferably is accomplished by balanced autoclaving of the sealed package and its contents, typically at temperatures of about 120° C. or higher. It has been found that autoclaving a contact lens packaged in a solution containing the polymer having mucin affinity effectively binds this polymer to the contact lens surface.

Such packaging solutions contain a second polymer, different from and in addition to, the first polymer having mucin affinity.

It is intended that the contact lens, once removed from the package solution, has the first polymer linked to its surfaces (for example, covalently linked), with the second polymer forming a layer on the first polymer. A primary purpose of the second polymer is to form a more wettable and/or more lubricious surface on the contact lens, as compared to a contact lens coated only with the first polymer. Thus, when the contact lens is first inserted in the eye, after removing the lens from the package solution, the contact lens is more wettable and/or more lubricious, and thus, more comfortable to wear. Over time, as the contact lens is worn, the second polymer will be removed from the contact lens, due to tear film flow and blinking, thus exposing the first polymer to eye tissue and tear film and leading to binding of mucin thereto.

As an example, immediately upon removing the contact lens from the packaging solution, a boronic acid copolymer is covalently linked to the contact lens surface, with the second polymer adsorbed by the boronic acid copolymer and any exposed contact lens surface. The second polymer provides improved comfort upon insertion of the contact lens in the eye. After wearing the lens for several hours, the second polymer is removed from the contact lens, whereby mucin begins binding to the boronic acid moiety of the boronic acid copolymer.

This invention also recognized that autoclaving a contact lens packaged in a solution comprising the first and second polymers in admixture will effectively bind the first polymer to the contact lens surface, with the second polymer being adsorbed on the lens coated with the first polymer. In other words, it is unnecessary to bind the first polymer, and then coat with the second polymer, in separate steps. When the solution containing this admixture is a contact lens package solution, any excess first polymer not linked to the contact lens surface, and any excess second polymer not adsorbed on to the contact lens, remaining in the packaging solution may be discarded.

Accordingly, the first polymer should have greater affinity for binding mucin than does the second polymer. Additionally, the first polymer should have greater affinity for binding the contact lens surface than does the second polymer, so that the second polymer does not unduly compete with the first polymer in binding to the contact lens surface. The second polymer should be non-permanently absorbed on to the contact lens surface, so that it is removed during contact lens wear to permit the first polymer to adsorb epithelial mucin. Additionally, the second polymer should be hydrolytically and oxidatively stable. Generally, the second polymer will be more wettable by tear film, and more lubricious, than the first polymer.

A wide variety of polymeric materials may be employed as the second polymer. Representative second polymers include: cellulosic materials, including hydroxypropylmethyl cellulose (HPMC), hydroxyethylcellulose, hydroxypropylcellulose and methyl cellulose; polyvinylpyrrolidone (PVP) and copolymers thereof, including PVP homopolymers (especially with a molecular weight of at least $1 \times 10^6$ Daltons), co-PVP-vinyl laurate, and co-PVP-glycidyl methacrylate (GMA); poly(2-ethyl-2-oxazoline); and polyethylene oxide (PEO)/polypropylene oxide (PPO) block copolymers, especially poloxamers or poloxamines, including those available from BASF under the tradenames Pluronic™ F38, Pluronic™ F127 and Tetronic™ 1107. The poloxamers and poloxamines include those disclosed in U.S. Pat. No. 6,440,366.

As mentioned, the first polymer (for example, the boronic acid-containing polymer) may be linked to the contact lens surface with an intermediate polymer. An example of such an intermediate polymer is a copolymer of DMA/GMA. In this case, the intermediate polymer may be included as a third polymer component in the packaging solution. Alternately, this intermediate polymer may be linked to the contact lens surface, prior to placing the contact lens in its packaging solution.

According to preferred embodiments, both the first and second polymers are included in a packaging solution. The packaging solution preferably comprises 0.0001 to 5 weight percent of the first polymer, more preferably 0.001 to 1 weight percent, and most preferably 0.01 to 0.1 weight percent. The packaging solution preferably comprises 0.001 to 10 weight percent of the second polymer, more preferably 0.01 to 5 weight percent, most preferably 0.1 to 1 weight percent. The package solutions preferably have an osmolality of at least about 200 mOsm/kg and a pH in the range of about 6 to about 8, and preferably about 6.5 to about 7.8.

Preferably, the sealed container is a hermetically sealed blister-pack, in which a concave well containing a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

Suitable buffers may optionally be added, such as: phosphate; borate (such as a mixture of boric acid and sodium borate); citrate; carbonate; tris-(hydroxymethyl)aminomethane (TRIS); bis(2-hydroxyethyl)-imino-tris-(hydroxymethyl)aminoalcohol (bis-tris); zwitterionic buffers such as N-[2-Hydroxy-1,1-bis(hydroxymethyl)ethyl]glycine (Tricine) and N-[2-Hydroxy-1,1-bis(hydroxymethyl)ethyl] glycine, MOPS; N-(Carbamoylmethyl)taurine (ACES); amino acids and amino acid derivatives, such as diglycine; and mixtures thereof. Generally, when present, buffers will be used in amounts ranging from about 0.05 to about 2.5 percent by weight, and preferably from about 0.1 to about 1.5 percent by weight of the solution.

If needed, the solutions of the present invention may be adjusted with tonicity agents, to approximate the osmotic pressure of normal lacrimal fluids which is equivalent to a 0.9 percent solution of sodium chloride or 2.5 percent of glycerol solution. The solutions may be made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which may cause stinging and eye irritation. Examples of suitable tonicity adjusting agents include, but are not limited to, sodium and potassium chloride, dextrose, calcium and magnesium chloride and the like and mixtures thereof. When present, these agents are typically used individually in amounts ranging from about 0.01 to about 2.5% w/v and preferably from about 0.2 to about 1.5% w/v. Preferably, the packaging solutions have an osmotic value of at least about 200 mOsm/kg, preferably from about 200 to about 450 mOsm/kg, more preferably from about 250 to about 400 mOsm/kg, and most preferably from about 280 to about 370 mOsm/kg, optionally employing a tonicity adjusting agent if needed to achieve these osmotic values.

The packaging solutions may further comprise a chelating agent, such as ethylenediamine tetraacetic acid (EDTA). When present, the chelating agent may be included at 0.0001 to 5 weight percent of the first polymer, more preferably 0.001 to 1 weight percent, and most preferably 0.01 to 0.1 weight percent.

The following examples illustrate various preferred embodiments of this invention.

Example 1

Synthesis of Boronic Acid-Containing Polymer

To a 1-L 3-neck round bottom flask containing a magnetic stir bar, water-cooled condenser and thermocouple is added approximately 0.2-wt % AIBN initiator (based on total weight of monomers), 5.0-mol % of 4-vinylphenylboronic acid (SBA), 10-mol % of methacrylic acid (MAA), 20-mol % of N-[(3-dimethylamino)propyl]methacrylamide (DMAPMA) and 65-mol % of N,N-dimethylacrylamide (DMA). The monomers and initiator are dissolved by addition of 300-mL of methanol to the flask. The solution is sparged with argon for at least 10-min. before gradual heating to 60° C. Sparging is discontinued when the solution reaches 40 to 45° C. and the flask is subsequently maintained under argon backpressure. Heating is discontinued after 48 to 72 hours at which point the cooled solution is added dropwise to 6 L of mechanically stirred ethyl ether. The precipitate is isolated either by filtration or decanting off the ether. The solid is dried in vacuo at 80° C. for a minimum of 18 hours and reprecipitated by dissolution in 300-mL methanol and dropwise addition into 6-L of stirred ethyl ether. The final polymer mass is determined after vacuum drying at 80° C. to a constant mass.

Examples 2-14

Synthesis of Boronic Acid-Containing Polymers

The polymers in Table 1 were synthesized according to the general procedure of Example 1, by varying the molar amounts and various monomers. The following additional designations are used in Table 1:

APMA 3-aminopropylmethacrylamide.HCl
AEMA 2-aminoethyl methacrylate
DMAEMA N-[(2-dimethylamino)ethyl]methacrylate
DMAPMA N-[(3-dimethylamino)propyl]methacrylamide
MAAPBA 3-methacrylamidophenylboronic acid

TABLE 1

|  | Ex 1 | Ex 2 | Ex 3 | Ex 4 | Ex 5 | Ex 6 | Ex 7 |
|---|---|---|---|---|---|---|---|
| DMA (mol %) | 65 | 50 | 55 | 40 | 65 | 68.5 | 70 |
| DMAPMA (mol %) | 20 | 30 | 25 | 20 | — | 19 | — |
| DMAEMA (mol %) | — | — | — | — | 20 | — | 20 |
| MAA (mol %) | 10 | 10 | 10 | 30 | 10 | — | — |
| APMA (mol %) | — | — | — | — | — | 7.5 | — |
| SBA (mol %) | 5 | 10 | 10 | 10 | 5 | 5 | 5 |

TABLE 1-continued

| AEMA (mol %) | — | — | — | — | — | — | 5 |
|---|---|---|---|---|---|---|---|
|  | Ex 8 | Ex 9 | Ex 10 | Ex 11 | Ex 12 | Ex 13 | Ex 14 |
| DMA (mol %) | 70 | 70 | 65 | 65 | 70 | 85 | 85 |
| DMAPMA (mol %) | 20 | 20 | 15 | 10 | 16 | 10 | 10 |
| MAA (mol %) | — | 7.5 | — | — | 7 | — | — |
| APMA (mol %) | 7.5 | — | 10 | 10 | — | — | — |
| SBA (mol %) | — | — | 10 | 15 | 7 | 5 | — |
| MAAPBA (mol %) | 2.5 | 2.5 | — | — | — | — | 5 |

Example 15

Coating of Contact Lenses with Boronic Acid-Containing Polymers

Contact lenses made of balafilcon A were cast and stored in borate buffer solution (BBS). Balafilcon A is a copolymer comprised of 3-[tris(tri-methylsiloxy)silyl]propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. The lenses were not plasma treated, and these lenses are designated as "No Plasma Control" in the following tables. Other balafilcon A lenses were plasma treated, and are designated "PV Control", below.

Some lenses of this batch were desalinated in deionized water, dried and subjected to successive plasma regimens of ammonia, butadiene and ammonia. Some lenses retained as further controls are designated "ABA Control" in the following tables.

For coating with the subject polymers, each ABA treated lens was placed in a glass scintillation vial containing 1.5-mL of a 2% (w/v) solution of the subject polymer dissolved in deionized water or phosphate buffered saline and 1.5 mL of a 1% (w/v) solution of DMA/GMA copolymer (86/14 mol/mol) in deionized water. The vials were capped and placed in a forced-air oven heated to 90° C. for 2 hours. After cooling, the coating solution was removed by aspiration and replaced with 20-mL of deionized (DI) water with shaking. After two additional aspiration/irrigation cycles, the lenses were sealed in polypropylene contact lens blister packs in BBS. The blister packs were autoclaved at 121° C. for 30-min.

Table 2 reports various surface properties of several coated samples and controls. Coated sample 1 was coated with the polymer of Example 1, and Coated sample 2 was coated with the polymer of Example 9. Atomic concentrations were determined by XPS, as described below. Contact angle was determined as described below.

TABLE 2

|  | XPS Atomic Concentrations | | | | Contact Angle |
|---|---|---|---|---|---|
|  | % C | % O | % N | % Si | (Water) |
| Coated Sample 1 | 69.6 +/− 0.6 | 17.1 +/− 0.4 | 11.3 +/− 0.6 | 0.3 +/− 0.1 | 73/81 |
| ABA Control 1 | 67.4 +/− 3.7 | 17.8 +/− 1.9 | 8.4 +/− 0.6 | 6.1 +/− 2.2 | 83/75 |
| No Plasma Control 1 | 60.2 +/− 0.4 | 21.3 +/− 0.3 | 7.6 +/− 0.4 | 10.9 +/− 0.6 | 115/117 |
| Coated Sample 2 | 70.2 +/− 1.7 | 16.5 +/− 0.8 | 11.9 +/− 0.5 | 0.7 +/− 0.2 | 47/40 |

TABLE 2-continued

| | XPS Atomic Concentrations | | | | Contact Angle (Water) |
|---|---|---|---|---|---|
| | % C | % O | % N | % Si | |
| ABA Control 2 | 64.8 +/− 4.8 | 19.4 +/− 2.4 | 7.7 +/− 1.0 | 7.7 +/− 1.4 | 94/74 |
| No Plasma Control | 59.4 +/− 0.3 | 22.1 +/− 0.2 | 7.1 +/− 0.2 | 11.3 +/− 0.2 | 111/115 |

X-Ray Photoelectron Spectroscopy (XPS) Analysis

XPS data was collected using a Physical Electronics Quantera SXM Scanning ESCA Microprobe. This instrument utilizes a monochromatic A1 anode operated at 18 kV and 100 Watts in the high power mode and 15 kV and 0.25 Watts/micron in low power mode. All high power acquisitions are rastered over a 1400 micron×100 micron analysis area. Dual beam neutralization (ions and electrons) is used. The base pressure of the instrument was $5\times10^{-10}$ torr and during operation the pressure was less than or equal to $1\times10^{-7}$ torr. This instrument made use of a hemispherical analyzer operated in FAT mode. A gauze lens was coupled to a hemispherical analyzer in order to increase signal throughput. Assuming the inelastic mean free path for a carbon 1s photoelectron is 35 Å, the practical measure for sampling depth for this instrument at a sampling angle of 45 is approximately 75 Å. The governing equation for sampling depth in XPS is:

$$\theta\lambda \sin 3 = d$$

where d is the sampling depth, λ is the photoelectron inelastic mean free path and θ is the angle formed between the sample surface and the axis of the analyzer. Each specimen was analyzed utilizing a low-resolution survey spectra (0-1100 eV) to identify the elements present on the sample surface. Quantification of elemental compositions was completed by integration of the photoelectron peak areas. Analyzer transmission, photoelectron cross-sections and source angle correction were taken into consideration in order to give accurate atomic concentration values.

Contact Angle Analysis

The instrument used for measurement was a Video Contact Angle System (VCA) 2500XE, (AST Products, Inc., Billerica, Mass., USA). This instrument utilizes a low-power microscope that produces a sharply defined image of the water drop, which is captured immediately on the computer screen. HPLC water is drawn into the VCA system microsyringe, and a 0.6 μl drop is dispensed from the syringe onto the sample. The contact angle is calculated by placing five markers along the circumference of the drop. The software of the system calculates a curve representing the circumference of the drop and the contact angle is recorded. Both a right and left contact angle are reported for each measurement in Table 2.

Protein Uptake Analysis

Table 3 reports protein uptake of lenses. The sample and control lenses were coated individually using a protein deposition solution (515 ppm standard) containing lysozyme. Glass vials containing 0.75 mL of deposition solution and individual lenses were placed into a 37° C. oven. After incubating for twenty-four hours, the vials containing the lenses were removed from the oven. Each lens was removed from the vial using tweezers and rinsed with saline solution. The deposition solution/standard, and the solution in which the lenses were incubated, were run by liquid chromatography (LC). The average of each set of lenses was established and the difference between the deposition solution and the lens incubation solution calculated. The same procedure was applied to the sample lenses. LC analysis was conducted using an Agilent 1100 Series Liquid Chromatograph, with the following instrument parameters:

| | |
|---|---|
| Column: | 4.6 mm × 150 mm Zorbax 300SB-C5, 5μ particle size |
| Mobile Phase A: | 95% HPLC Water/5% HPLC Acetonitrile with 0.1% TFA |
| Mobile Phase B: | 95% HPLC Acetonitrile/5% HPLC Water with 0.1% TFA |
| Gradient: | 85% A to 47% A over 20 minutes, reset to initial conditions, hold 10 minutes |
| Flow Rate: | 1 mL/minute |
| Injection Volume: | 10.0 μL |
| UV Detection: | 215 nm |

TABLE 3

| | Protein Uptake (μg/lens) |
|---|---|
| Coated Sample 1 | 23 +/− 4 |
| Coated Sample 2 | 20 +/− 1 |
| PV Control | 20 +/− 4 |

Example 16

Mucin Affinity

Mucin affinity was evaluated using an enzyme linked lectin assay. This assay utilizes biotinylated jacalin as a probe for detection of mucin on the contact lens surface. The strong biotin-streptavidin interaction provides the base for further signal amplification using a streptavidin-peroxidase conjugate.

Coated Samples 1 and 2 from Example 15 were evaluated, as well as two controls, PV Control and No Plasma Control from Example 15.

To test the mucin affinity of the contact lens material, purified Bovine Submaxillary Gland Mucin (BSM) was used. The mucin solution was prepared at 0.5 mg/ml using a 20 mM PBS buffer (PBS20; pH 7.4; Na/K=33). The contact lenses were stored at room temperature prior to analysis. First, the lenses were washed with PBS20 and transferred with a tweezer to a vial containing the mucin solution. Incubation with the coating solution proceeded over night at room temperature. Remaining uncoated spots on the samples were blocked using the synthetic surfactant Pluronic F108. Biotinylated jacalin was added to each vial and the samples were incubated at room temperature. This was followed by addition of streptavidin-peroxidase conjugate. Relative amount of bound mucin was quantified by the addition of substrate, followed by measurement of the degradation product at 405 nm. It was determined that the coated samples had greater affinity for mucin than for lysozyme.

Example 17

PureVision® contact lenses (Bausch & Lomb Incorporated, Rochester, N.Y. USA) were provided. These contact lenses are made of balafilcon A copolymer, and have a silicate-containing surface from plasma treatment in an oxygen-containing environment. Lenses were placed in contact lens blister packages containing borate buffered saline (BBS) and the following additional components:

|  | Control | Package Solution A | Package Solution B |
|---|---|---|---|
| Boronic Acid Polymer of Example 1 | — | 0.03 wt % | 0.06 wt % |
| HPMC | — | 0.01 wt % | — |

The packages were sealed with lidstock, and then autoclaved 30 minutes at 121° C. Lenses were removed from the package and inspected. The contact lenses packaged in Solution A (BBS, Boronic Acid Polymer and HPMC) were noticeably more lubricious than those packaged in Solution B (BBS, Boronic Acid Polymer, and no HPMC). However, after one to four hours of wearing the contact lens, the HPMC will be removed from the lens, allowing epithelial mucin to bind to the boronic acid copolymer.

Example 18

Copolymer of DMA/GMA (86/14 mol/mol)

The DMA/GMA copolymer of Example 15 was prepared by the following procedure. To a 1 L reaction flask were added distilled N,N-dimethylacrylamide (DMA, 48 g, 0.48 moles), distilled glycidyl methacrylate (GMA, 12 g, 0.08 moles) Vazo 64 initiator (AIBN, 0.1 g, 0.0006 moles) and anhydrous tetrahydrofuran (500 ml). The reaction vessel was fitted with a mechanical stirrer, condenser, thermal controller and a nitrogen inlet. Nitrogen was bubbled through the solution for 15 minutes to remove any dissolved oxygen. The reaction flask was then heated to 40° C. under a passive blanket of nitrogen for 168 hours. The reaction mixture was then added slowly to ethyl ether (1.5 L) with good mechanical stirring. The reactive polymer precipitated and organic solvents were decanted off. The solid was collected by filtration and placed in a vacuum oven to remove the ether leaving 58.2 g of reactive polymer (97% yield). The reactive polymer was placed in a desiccator for storage until use.

Examples 19-22

PureVision® contact lenses (Bausch & Lomb Incorporated, Rochester, N.Y. USA) were provided. These contact lenses are made of balafilcon A copolymer, and have a silicate-containing surface from plasma treatment in an oxygen-containing environment. Lenses were placed in contact lens blister packages containing borate buffered saline (BBS) with the following additional components, where "ppm" designates parts per million (by weight):

|  | Example 19 | Example 20 | Example 21 | Example 22 |
|---|---|---|---|---|
| Boronic Acid Polymer | Example 13 | Example 14 | Example 1 | Example 1 |
|  | 500 ppm | 500 ppm | 500 ppm | 500 ppm |
| HPMC | 2500 ppm | 2500 ppm | 2500 ppm | 2500 ppm |
| EDTA | 300 ppm | 300 ppm | — | 300 ppm |

The packages were sealed with lidstock, and then autoclaved 30 minutes at 121° C.

Having thus described various preferred embodiment of the invention, those skilled in the art will appreciate that various modifications, additions, and changes may be made thereto without departing from the spirit and scope of the invention, as set forth in the following claims.

We claim:

1. A contact lens having its surfaces coated with an inner layer and an outer layer, the inner layer comprising a first polymer having affinity for mucin, and the outer layer comprising a second polymer different from the first polymer, wherein the contact lens is so constructed that the outer layer is removed from the inner layer while the contact lens is worn.

2. A contact lens having its surfaces coated with an inner layer and an outer layer, the inner layer comprising a first polymer having affinity for mucin, and the outer layer comprising a second polymer different from the first polymer, the contact lens further comprising a layer intermediate the inner layer and the contact lens surface and containing a third polymer different from the first and second polymers.

3. The contact lens of claim 1, wherein the first polymer has greater affinity to mucin than to the second polymer.

4. The contact lens of claim 1, wherein the first polymer has greater affinity to surfaces of the contact lens than does the second polymer.

5. The contact lens of claim 1, wherein the outer layer is adsorbed on the contact lens coated with the inner layer.

6. A contact lens having its surfaces coated with an inner layer and an outer layer, the inner layer comprising a first polymer having affinity for mucin, and the outer layer comprising a second polymer different from the first polymer, wherein the first polymer comprises monomeric units derived from an ethylenically unsaturated monomer containing a boronic acid moiety, and wherein the contact lens is so constructed that the second polymer is removed from the contact lens while the contact lens is worn and the boronic acid moieties complex with mucin.

7. The contact lens of claim 6, wherein the first polymer comprises monomeric units derived from at least one member selected from the group consisting of: a vinylphenyl boronic acid and a methacrylamido phenyl boronic acid.

8. The contact lens of claim 6, wherein the first polymer further comprises monomeric units derived from an ethylenically unsaturated monomer containing a tertiary-amine moiety.

9. The contact lens of claim 6, wherein the first polymer is a copolymer comprising: monomeric units derived from an ethylenically unsaturated monomer containing a boronic acid moiety; and monomeric units derived from an ethylenically unsaturated monomer containing a moiety reactive with complementary reactive functionalities at the lens surface.

10. The contact lens of claim 1, wherein the second polymer includes at least one member selected from the group consisting of: cellulosic materials; polyvinylpyrrolidone and copolymers thereof; poly(2-ethyl-2-oxazoline) and copolymers thereof; and polyethylene oxide/polypropylene oxide block copolymers.

11. The contact lens of claim 1, wherein the first polymer is covalently linked to the lens surface through primary amine or hydroxyl radicals at the lens surface.

12. A contact lens having its surfaces coated with an inner layer and an outer layer, the inner layer comprising a first polymer having affinity for mucin, and the outer layer comprising a second polymer different from the first polymer, wherein the first polymer is permanently bound to the contact lens, and the second polymer is temporarily bound to the contact lens.

13. The contact lens of claim 12, further comprising a layer intermediate the inner layer and the contact lens surface and containing a third polymer different from the first and second polymers.

14. The contact lens of claim 12, wherein the contact lens is so constructed that the outer layer is removed from the inner layer while the contact lens is worn.

15. The contact lens of claim 12, wherein the first polymer has greater affinity to mucin than to the second polymer.

16. The contact lens of claim 12, wherein the first polymer has greater affinity to surfaces of the contact lens than does the second polymer.

17. The contact lens of claim 12, wherein the outer layer is adsorbed on the contact lens coated with the inner layer.

18. The contact lens of claim 12, wherein the first polymer comprises monomeric units derived from an ethylenically unsaturated monomer containing a boronic acid moiety.

19. The contact lens of claim 18, wherein the first polymer comprises monomeric units derived from at least one member selected from the group consisting of: a vinylphenyl boronic acid and a methacrylamido phenyl boronic acid.

20. The contact lens of claim 18, wherein the first polymer further comprises monomeric units derived from an ethylenically unsaturated monomer containing a tertiary-amine moiety.

21. The contact lens of claim 18, wherein the first polymer is a copolymer comprising: monomeric units derived from an ethylenically unsaturated monomer containing a boronic acid moiety; and monomeric units derived from an ethylenically unsaturated monomer containing a moiety reactive with complementary reactive functionalities at the lens surface.

22. The contact lens of claim 12, wherein the second polymer includes at least one member selected from the group consisting of: cellulosic materials; polyvinylpyrrolidone and copolymers thereof; poly(2-ethyl-2-oxazoline) and copolymers thereof; and polyethylene oxide/polypropylene oxide block copolymers.

23. The contact lens of claim 12, wherein the first polymer is covalently linked to the lens surface through primary amine or hydroxyl radicals at the lens surface.

24. The contact lens of claim 18, wherein the contact lens is so constructed that the second polymer is removed from the contact lens while the contact lens is worn and the boronic acid moieties complex with mucin.

* * * * *